United States Statutory Invention Registration [19]

[11] Reg. Number: H989

Hartman [43] Published: Nov. 5, 1991

[54] PURIFICATION OF HYDROLYZED PROTEIN BY EXTRACTION

[75] Inventor: Guy J. Hartman, Decatur, Ill.

[73] Assignee: A. E. Staley Manufacturing Co., Decatur, Ill.

[21] Appl. No.: 552,403

[22] Filed: Jul. 13, 1990

[51] Int. Cl.[5] ..... C07K 3/12; C07K 3/00

[52] U.S. Cl. ..... 530/422; 530/350; 530/370; 530/407; 530/412; 530/423; 530/378; 530/425

[58] Field of Search ..... 530/350, 370, 412, 414, 530/418, 419, 420, 427, 407

[56] References Cited

U.S. PATENT DOCUMENTS

| | | | |
|---|---|---|---|
| 2,991,309 | 7/1961 | Hoglan et al. | 530/407 |
| 4,165,391 | 8/1979 | Corbett | 426/580 |
| 4,644,067 | 2/1987 | Weber et al. | 548/497 |
| 4,759,944 | 7/1988 | Fasi et al. | 426/650 |

FOREIGN PATENT DOCUMENTS

| | | |
|---|---|---|
| 0361595 | 4/1990 | European Pat. Off. . |
| 0361596 | 4/1990 | European Pat. Off. . |
| 0361597 | 4/1990 | European Pat. Off. . |
| 0363771 | 4/1990 | European Pat. Off. . |

OTHER PUBLICATIONS

Robinson et al., J. High Resolut. Chromatogr. Chromatogr. Commun., vol. 10(1), pp. 6–11 (1987).

Oosthuizen et al, Ann. Clin. Biochem., vol. 22, No. 4, pp. 402–407 (1985).

Hurst et al., Int. J. Vitam. Nutr. Res., vol. 53, No. 3, pp. 239–242 (1983) (abstract).

J. Velisek et al., "Chlorohydrins in Protein Hydrolysates", *Z. Lebensm. Unters. Forsch.*, vol. 167, pp. 241–244 (1978).

T. C. Lo and M. H. I. Baird, "Extraction, Liquid–Liquid", *Encyclopedia of Chemical Technology*, vol. 9, pp. 672–721 (Kirk–Othmer, eds., John Wiley & Sons, Inc., N.Y., N.Y., 3rd ed., 1980).

K. Johnston, "Supercritical Fluids", *Encyclopedia of Chemical Technology*, Supp. vol., pp. 872–893 (Kirk–Othmer, eds., John Wiley & Sons, Inc., N.Y., N.Y., 3rd ed., 1984).

A. Seidell, "Ethyl Acetate", *Solubilities of Organic Compounds*, pp. 246 and 247 (D. Van Nostrand Company, Inc., 1941).

"Supercritical Processes Win CPI Acceptance", *Chemical Engineering*, pp. 37 and 39 (Jul. 1989).

*Primary Examiner*—John S. Maples
*Assistant Examiner*—Shean C. Wu

[57] ABSTRACT

A method of purifying hydrolyzed protein compositions by contact with a substantially phase-incompatible fluid extractant is provided. A reduction in the concentration of chlorohydrins, measured as 3-monochloro-1,2-propanediol, in hydrolyzed protein compositions can be obrtained by contacting the hydrolyzed protein composition with such a phase-incompatible fluid extractant, e.g., ethyl acetate. The method allows removal of chlorohydrins without substantially affecting the organoleptic qualities of the hydrolyzed protein.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PURIFICATION OF HYDROLYZED PROTEIN BY EXTRACTION

FIELD OF INVENTION

This invention relates to a method of purifying hydrolysed protein compositions useful as food ingredients.

BACKGROUND OF THE INVENTION

The hydrolysis of proteins to produce food ingredients is well known. For example, U.S. Pat. No. 4,165,391 (Corbett) discusses the use of hydrolysed vegetable proteins (HVP) as flavoring agents for providing meaty flavor and/or flavor intensity to foods. Corbett notes that acid hydrolysis of vegetable proteins is the most important method (as compared with enzymic hydrolysis and alkaline hydrolysis) from the standpoint of food products and that hydrochloric or sulfuric acid is generally used in the hydrolysis.

The use of hydrochloric acid in the hydrolysis of proteins has bee implicated in the production of chlorohydrins from residual glycerol in the protein source. J. Velisek et al., "Chlorohydrins in Protein Hydrolysates", *Z. Lebensm. Unters. Forsch,* vol. 167, pp. 24–44 (1978). Methods of removing chlorohydrins or preventing their formation are discussed in U.S. Pat. No. 4,759,944 (Fasi et al.). Fasi et al. state that preventing the formation of chlorohydrins is impractical without altering the organoleptic qualities (e.g., taste) of the hydrolysed protein. Likewise, decolorizing with carbon or rectification (i.e., fractional distillation) to remove chlorohydrins are characterized as impractical. Fasi et al. disclose a method for removing chlorohydrins from hydrolysed protein which involves subjecting the hydrolysed protein to steam distillation under reduced pressure while keeping the density of the hydrolysed protein substantially constant.

European Patent Application No. 89202368.0, filed Sept. 20, 1989, and published Apr. 4, 1990, as E.P.O. Publication No. 0361596, disclosed a method of hydrolysing protein with hydrochloric acid. It is stated that the reaction is initially carried out at between 60° C. and 97° C. and that the reaction temperature is further increased to 100° C. to 110° C. and held prior to cooling and neutralizing. It is also stated that a further reduction in the amount of chloropropanols in the hydrolysate may be obtained by steam distillation or gel filtration or by hydrolysis of chloropropanols.

European Patent Application No. 89202369.8, filed Sept. 20, 1989, and published Apr. 4, 1990, as E.P.O. Publication No. 0361597, discloses subjecting an aqueous solution of hydrochloric acid-hydrolysed protein to gel permeation chromatography using a porous material having an equivalent pore diameter between 0.5 and 2.0 nanometers and eluting a fraction which is free of detectable amounts of chloropropanols.

European Patent Application No. 89202367.2, filed Sept. 20, 1989, and published Apr. 4, 1990, as E.P.O. Publication No. 0361595, discloses a process for improving a hydrochloric acid-hydrolysed protein by subjecting an aqueous solution thereof to the conditions which cause hydrolysis of chloropropanols therein, e.g., a pH between 5.5 and 8.0 and a temperature between 20° C. and 180° C. for a period of between 10 days to 15 minutes.

European Patent Application No. 89118189.3, filed Sept. 30, 1989, and published Apr. 18, 1990, as E.P.O. Publication No. 0363771, discloses a process for the production of a hydrolysed protein using hydrochloric acid wherein the hydrolysate is treated with alkali and held at a pH of from 8 to 14 to reduce the amount of undesirable chlorinated compounds.

SUMMARY OF INVENTION

This invention relates to a method of purifying a hydrolysed protein comprising contacting a mixture of a hydrolysed protein and a chlorohydrin with a substantially phase-incompatible fluid extractant capable of extracting at least a portion of said clorohydrin from said mixture and separating said hydrolysed protein from said phase-incompatible fluid extractant.

This invention also relates to a method of preparing hydrolysed proteins useful as food ingredients comprising hydrolysing a protein in an aqueous medium at an acidic pH, said aqueous medium additionally comprising chloride and a member selected from the group consisting of glycerol and precursors thereof, to produce a hydrolysed protein, contacting said hydrolysed protein with a substantially phase-incompatible fluid extractant capable of extracting at least a portion of said chlorohydrin from said hydrolysed protein, and separating said incompatible fluid extractant from said hydrolysed protein.

It has been found that extraction with a substantially phase-incompatible fluid extractant can be used to remove chlorohydrins from hydrolysed protein.

DETAILED DESCRIPTION OF THE INVENTION

The hydrolysed protein compositions which can be advantageously treated in accordance with this invention will generally contain small, but measurable, amounts of chlorohydrins, e.g., k3-monochloro-1,2-propanediol (MCP) and 1,3-dichloro-2-propanol (DCP). As used herein, the term chlorohydrins shall be used to denote the chlorinated products of the reaction glycerol with chloride in the presence of acid. Thus, the term "chlorohydrins" includes not only DCP, but 2-monochloro-1,3-propanediol, and 2,3-dichloro-1-propanol as well. However, as used herein, the term "chlorohydrin concentration" shall refer to, unless noted otherwise in context, the concentration of MCP measured as described below.

The hydrolysed protein compositions are prepared by the acid hydrolysis of a proteinaceous material. Commonly available proteinaceous materials generally contain glycerol and/or a precursor thereof, e.g., a fatty triglyceride. To obtain superior organoleptic qualities, hydrochloric acid is generally employed in the acid hydrolysis of the proteinaceous material. Accordingly, glycerol and chloride are available in the presence of acid and thus react to form chlorohydrins during hydrolysis of the protein.

The precise concentration of chlorohydrins in the hydrolysed protein will vary according to the nature of the proteinaceous material (e.g., the concentration of glycerol and precursors thereof) and hydrolysis conditions chosen (e.g., the concentrations of chloride and water in the hydrolysis medium). Typical chlorohydrin concentrations, measured by gas chromatography as MCP, will typically range from about 50 to 500 parts per million of the hydrolysed protein composition.

The source of the proteinaceous material from which the hydrolysed protein is derived may vary widely.

Proteins from animal sources (e.g., beef extract from beef and fish protein meal from fish) or microbial sources (e.g., dried distillers solubles from yeast) may be hydrolysed. Typically, however, the hydrolysed protein will be hydrolysed vegetable protein (HVP) obtained by the hydrolysis of a vegetable protein material. Such materials should generally contain greater than 25% by weight protein (as measured by Kjeldahl nitrogen analysis). Examples of sources of vegetable protein materials include wheat gluten, corn gluten, extracted soy flour, soy protein concentrates, peanut flour, peanut protein concentrate, extracted cottonseed meal, cottonseed protein concentrate, and extracted canola (i.e., low erucic acid rapeseed) meal. The proteins may be used singly or in various combinations.

The hydrolysis of the proteinaceous material is accomplished by treating the material with aqueous acid, for example by conventional acid hydrolysis using 2N to 12N hydrochloric acid, or its equivalent. The preferred normality of the acid for hydrolysis is 4N to 6N. Typically, 6N hydrochloric acid is heated to 60° C. to 90° C., preferably 110° C. to 120° C., in a steam jacketed, glass-lined or enameled reaction kettle equipped with an agitator. Protein material (e.g., in an amount, by weight, about 50% greater than the hydrochloric acid) is next added to the hot hydrochloric acid and heating is continued under reflux with continuous stirring for 2 to 10 hours, preferably about 5 to 6 hours. The degree of hydrolysis may vary, but will typically result in a product in which at least 80% of the amine nitrogen is present as free amine. The resulting hydrolysed protein may be filtered to remove insolubles, primarily humin, and the filtered material discarded. This first filtration can be accomplished before or after substantial neutralization of the hydrolysed protein with concentrated alkali, typically sodium carbonate. The hydrolysed protein may then be allowed to age, e.g., for a few days to a few weeks, in order to allow separation of slowly crystallizing substances and slowly agglomerating colloidal particles by filtration or other physical means. The hydrolysed protein may optionally be decolorized with activated carbon by conventional methods, either before or after contacting as discussed below.

Just prior to the contacting step, the hydrolysed protein will typically be in one of three forms, i.e., a liquid (an aqueous solution at, e.g., 35%–45% by weight dry solids), a paste (an aqueous slurry at, e.g., 70%–90% by weight dry solids) or a solid (e.g., at up to about 5% moisture). The choice of a particular form of the hydrolysed protein may affect the efficiency and/or utility of the precise means of contacting and separating and the choice of fluid extractant, as more fully discussed below.

The purification accomplished by this invention involves contacting the hydrolysed protein with a substantially phase-incompatible fluid extractant. This fluid is capable of extracting at least a portion of the chlorohydrins from the hydrolysed protein. By "substantially phase-incompatible" is meant a fluid that will form a phase that is separable from the hydrolysed protein. Such fluids include (i) materials that are liquids during the contacting and (ii) materials that are supercritical fluids during the contacting, e.g., carbon dioxide above both its critical temperature and critical pressure. The liquids can be further subdivided into two types: those which are "substantially immiscible" with the aqueous phase of a liquid hydrolysed protein and those which are merely non-solvents for the hydrolysed protein.

By "substantially immiscible" is meant a liquid which, when admixed with a hydrolysed protein to be extracted in roughly equal proportions, will coalesce into a liquid phase that is physically separable from the aqueous phase of a liquid hydrolysed protein. The principles and mechanics of liquid-liquid extraction are disclosed in T. C. Lo and M. H. I. Baird, "Extraction Liquid-Liquid", *Encyclopedia of Chemical Technology*, Vol. 9, pp. 672–721 (Kirk-Othmer, eds, John Wiley & Sons, Inc., N.Y., N.Y., 3d ed., 1980), the disclosure of which is incorporated by reference. That article discloses processes and apparatus that can be adapted to the practice of this invention by one of ordinary skill in this art. The substantially immiscible liquid extractant is preferably truly immiscible or only very sparingly soluble in the hydrolysed protein solution to eliminate or minimize the need to remove residual liquid extractant from the solution. An example of a substantially immiscible liquid extractant is ethyl acetate.

Liquids of the second type referred to above are miscible with water (if any) in the hydrolysed protein, but are non-solvents (when in admixture with such water) for the hydrolysed protein. By "non-solvent" is meant that a major portion by weight (i.e., at least 50% of the dry solids of the hydrolysed protein is present in a solid phase, and thus, will be recoverable by physical means (e.g., filtration, centrifugation, decatation and the like).

Also within the scope of this invention is the use of supercritical fluids as extractant. Supercritical fluid extraction is described by K. Johnston, "Super-critical Fluids", *Encyclopedia of Chemical Technology*, Supp. Vol., pp. 872–893 (Kirk-Othmer, eds., John Wiley & Sons, Inc., N.Y., N.Y., 3d ed., 1984), the disclosure of which is incorporated herein by reference. A typical supercritical fluid extractant is carbon dioxide at a temperature above its critical temperature and a pressure above its critical pressure.

The substantially phase-incompatible fluid extractant will also have a sufficient affinity for the chlorohydrins in the hydrolysed protein to cause the chlorohydrins to be extracted into the fluid extractant by mass action during the contacting step. Thus, the fluid extractant will have a balanced degree of polarity; i.e., a degree sufficient to extract the chlorohydrins from the hydrolysed protein solution but insufficient to form a single inseparable phase after contact with the hydrolysed protein. Preferred fluid extractants are food grade materials such that the presence of small amounts of residual fluid extractant in the hydrolysed protein solution would be acceptable. An especially preferred fluid extractant is ethyl acetate.

To extract the chlorohydrins from the hydrolysed protein solution, the substantially phase-incompatible fluid extractant and hydrolysed protein are placed in extractive contact (i.e., greater than minimal contact is induced between the extractant and aqueous protein phases). Such contact generally involves mixing of the fluid extractant with the hydrolysed protein. The conditions under which the hydrolysed protein is mixed with a liquid extractant generally involve ambient or mildly elevated temperature (e.g., 60° C. to 100° C. and elevated pressure if necessary to contain water or liquid extractant vapor). The conditions under which the hydrolysed protein is mixed with a supercritical fluid extractant will be chosen in accordance with the considerations discussed by Johnston, referred to above.

The amount of fluid extractant used is not critical, but the weight ratio of fluid extractant to hydrolysed protein solution generally ranges from about 1:1 to about 10:1, preferably about 2.5, depending, of course, upon the number of theoretical plates attainable with the chosen extractor and the desired extent of reduction of chlorohydrin level in the hydrolysed protein solution. The fluid extractant can be divided into a plurality of aliquots for multiple batch extractions of the reaction product (i.e., a multistage extraction) or it can be contacted with the hydrolysed protein solution in a continuous manner (e.g., cocurrent, crosscurrent or countercurrent) as more fully discussed below.

After being placed in extractive contact, the reaction product and fluid extractant are separated. Generally, the hydrolysed protein and the fluid extractant will separate, e.g., coalesce, into separate phases during the quiescent period following the cessation of mixing of the two components. A liquid extractant phase will typically have a lower density than an aqueous solution phase which will allow one to physically separate the two phases, e.g., decanting off the liquid extractant phase.

After separation, residual fluid extractant can be removed from the hydrolysed protein solution, but need not be removed if its presence is acceptable. The fluid extractant can be separated from the chlorohydrins, e.g., by stripping, distillation and/or evaporation. The isolated chlorohydrins can be destroyed by treatment with alkalis to produce glycerol and chloride salts.

In a typical process of this invention employing a substantially immiscible liquid extractant, a hydrolysed protein solution (at about 40% by weight solids) is fed into a first feed port (for a heavier liquid, near the top of a vertical, stirred, extractor column. The hydrolysed protein falls through the column while food grade ethyl acetate is fed to a second feed port (for a lighter liquid) near the base of the column. The ethyl acetate rises through the stirred column, i.e., countercurrent to the flow of the hydrolysed protein solution. In an unstirred portion of the column just below the second feed port, the ethyl acetate and hydrolysed protein solution separate and the hydrolysed protein solution is withdrawn from the column through a bottom exit port below this zone of separation. Likewise, in an unstirred portion of the column just above the first feed port, the ethyl acetate is withdrawn from the column through a top exit port.

The hydrolysed protein solution exiting the bottom of the column will be depleted with respect to chlorohydrins and can be subjected to solvent stripping to remove residual ethyl acetate. The stripped ethyl acetate can be sent to solvent recovery along with the chlorohydrin-enriched ethyl acetate exiting the column. The solvent recovery process may include distillation of the chlorohydrin-enriched ethyl acetate to collect purified ethyl acetate as a distillate (which can be recycled to the second feed port of the column) and a chlorohydrin mixture as bottoms. These bottoms can be treated with alkali (e.g., soda ash) to convert substantially all of the chlorohydrins to glycols and salts which are more amenable to safe and efficient waste treatment.

The extent of the reduction in chlorohydrin concentration in the hydrolysed protein will, of course, depend upon the extent of contact with the fluid extractant, i.e., the ratio of the amount of fluid extractant to that of the hydrolysed protein solution, and the precise efficiency of the fluid extractant under the given contact conditions. For example, it has been found that the extraction coefficient for contact of an approximately 40% solids hydrolysed protein solution with food grade ethyl acetate is about 0.42 with respect to 3-monochloro-1,2-propanediol. This means that a batch extraction of a ratio of about 1:1 will reduce the MCP level by about 42%. Generally, the fluid extractant will remove at least a significant portion of the chlorohydrins. By "significant" is meant more than a nominal amount, e.g., at least 10% by weight and preferably at least 30% by weight of the chlorohydrin in said hydrolysed protein.

The hydrolysed proteins can be analyzed for the presence of MCP by the method described in U.S. Pat. No. 4,759,944 (Fasi et al.), the disclosure of which is incorporated herein by reference. The results shown in the following examples were obtained in accordance with that method. All parts, percentages and ratios stated herein are by weight unless otherwise indicated.

EXAMPLES

A three-step extraction was performed using a separatory funnel. A soy protein hydrolysate at about 40% by weight solids and food grade ethyl acetate were added to the funnel at a total weight to volume ratio of 1:1 (gm:ml), respectively. The concentrations of 3-monochloro-1,2-propanediol (3-MCP) and 2-monochloro-1,3-propanediol (2-MCP) of the starting soy protein hydrolysate, ethyl acetate fraction (EA) and soy protein hydrolysate fraction (SPH) after each step, and the percent reduction of each after each step are shown below.

TABLE 1

| | | 3-MCP | | 2-MCP | |
|---|---|---|---|---|---|
| Step | Fraction | Amount (ppm by wt.) | Reduction in SHP (wt. %) | Amount (ppm by wt.) | Reduction in SHP (wt. %) |
| Starting | SPH | 71.2 | — | 9.86 | — |
| 1 | SPH | 43.2 | 39.3% | 6.99 | 29.1% |
| | EA | 26.5 | — | 2.76 | — |
| 2 | SPH | 24.2 | 44.0% | 3.44 | 50.8% |
| | EA | 11.4 | — | 1.31 | — |
| 3 | SPH | 13.9 | 42.6% | 5.30 | 42.2 |
| | EA | 5.3 | — | 0.69 | — |

Based on an extraction coefficient of 0.42, the level of 3-MCP in ppm after a successive series of theoretical plates was calculated for four different original levels of 3-MCP and the results are shown below.

TABLE 2

| Theoretical Plates | Level of 3-MCP (ppm by wt.) | | | |
|---|---|---|---|---|
| (Original) | 100 | 250 | 500 | 1,000 |
| 1 | 58 | 145 | 290 | 580 |
| 2 | 33.64 | 84.10 | 168.40 | 336.40 |
| 3 | 19.51 | 48.78 | 97.56 | 195.10 |
| 4 | 11.32 | 28.29 | 56.58 | 113.30 |
| 5 | 6.57 | 16.43 | 32.85 | 65.66 |
| 6 | 3.81 | 9.53 | 19.05 | 38.11 |
| 7 | 2.21 | 5.53 | 11.05 | 22.10 |
| 8 | 1.28 | 3.21 | 6.41 | 12.82 |
| 9 | 0.742 | 1.86 | 3.71 | 7.42 |
| 10 | 0.430 | 1.08 | 2.15 | 4.30 |
| 11 | 0.249 | 0.624 | 1.56 | 2.49 |
| 12 | 0.144 | 0.361 | 0.722 | 1.44 |
| 13 | 0.084 | 0.209 | 0.418 | 0.835 |
| 14 | 0.049 | 0.122 | 0.244 | 0.487 |
| 15 | 0.028 | 0.071 | 0.142 | 0.284 |
| 16 | 0.016 | 0.041 | 0.081 | 0.162 |
| 17 | 0.009 | 0.023 | 0.046 | 0.093 |
| 18 | 0.005 | 0.013 | 0.026 | 0.052 |
| 19 | 0.003 | 0.007 | 0.015 | 0.029 |

TABLE 2-continued

| Theoretical Plates | Level of 3-MCP (ppm by wt.) | | | |
|---|---|---|---|---|
| 20 | 0.002 | 0.004 | 0.009 | 0.017 |
| 21 | 0.001 | 0.003 | 0.006 | 0.012 |
| 22 | — | 0.002 | 0.004 | 0.007 |
| 23 | — | 0.001 | 0.002 | 0.005 |
| 24 | — | — | 0.001 | 0.002 |
| 25 | — | — | — | 0.001 |

What is claimed is:

1. A method of purifying a hydrolysed protein comprising contacting a mixture of a hydrolysed protein and a chlorohydrin with a substantially phase-incompatible fluid extractant capable of extracting at least a portion of said chlorohydrin from said aqueous mixture and separating said hydrolysed protein from said substantially phase-incompatible fluid extractant.

2. A method of claim 1 wherein said contacting is accomplished at a contact level and for a contact time sufficient to reduce the chlorohydrin concentration to no greater than about 1 ppm.

3. A method of claim 1 wherein said hydrolysed protein has a chlorohydrin content before said contacting of from about 50 ppm to 500 ppm and said contacting is sufficient to reduce the chlorohydrin level after said contacting to no greater than about 1 ppm.

4. A method of claim 1 further comprising removing at least a portion of said chlorohydrin from said substantially phase-incompatible fluid extractant after said separating.

5. A method of claim 1 wherein said substantially phase-incompatible fluid extractant is a substantially immiscible liquid.

6. A method of claim 1 wherein said substantially phase-incompatible fluid extractant is ethyl acetate.

* * * * *